US00PP15231P2

(12) United States Plant Patent
Hall

(10) Patent No.: US PP15,231 P2
(45) Date of Patent: Oct. 12, 2004

(54) ***LAVANDULA* PLANT NAMED 'THUMBELINA LEIGH'**

(50) Latin Name: *Lavandula angustifolia*
Varietal Denomination: Thumbelina Leigh

(76) Inventor: Elsie Hall, Leighvander, RD 1, Wairau Valley, Marlborough (NZ)

( * ) Notice: Subject to any disclaimer, the term of this patent is extended or adjusted under 35 U.S.C. 154(b) by 22 days.

(21) Appl. No.: 10/665,842

(22) Filed: Sep. 19, 2003

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database, 2003/05, GTI Jouve Retrieval Software, citation for 'Thumbelina Leigh'.*

* cited by examiner

*Primary Examiner*—Kent Bell
*Assistant Examiner*—S. B. McCormick-Ewoldt
(74) *Attorney, Agent, or Firm*—Mark P. Bourgeois

(57) ABSTRACT

A new cultivar of *Lavandula angustifolia* plant named 'Thumbelina Leigh' that is characterized by a compact rounded habit, violet-blue flowers, strong fragrance and repeat flowering. In combination, these traits set it apart from all other existing varieties of *Lavandula* known to the inventor.

2 Drawing Sheets

Botanical classification: *Lavandula angustifolia*.
Variety denomination: 'Thumbelina Leigh'.

BACKGROUND OF THE INVENTION

The present invention relates to a new and distinct cultivar of *Lavandula angustifolia* and hereinafter referred to by the cultivar name 'Thumbelina Leigh'. The new cultivar was discovered as a seedling growing in a bed of *Lavandula angustifolia* 'Hidcote' (not patented) in a cultivated area of Wairau Valley, Marlborough, New Zealand in 1993. However, since the bed was open pollinated in an area of other lavender varieties, the exact parents are unknown.

The new lavender plant 'Thumbelina Leigh' is distinct and unique due to its compact rounded habit, violet-blue flowers, strong fragrance and repeat flowering. The closest comparison plant is *Lavandula angustifolia* 'Lady' (not patented). 'Thumbelina Leigh' is distinguishable from 'Lady' by its smaller overall size, a darker green stem, cylindrical spike shape, purple calyx and more vigorous habit.

The new cultivar was first asexually propagated by cuttings in Wairau Valley, Marlborough, New Zealand by the inventor in 1993. Since that time subsequent generations have been determined fixed and stable.

SUMMARY OF THE INVENTION

The new lavender 'Thumbelina Leigh' is distinguished from all other known varieties of *Lavandula*, by the following characteristics:

1. Compact rounded habit.
2. Short compact flower spikes of violet-blue flowers.
3. A strong sweet fragrance.
4. Repeat flowering.

These unique traits set 'Thumbelina Leigh' apart from all other existing varieties known to the inventor.

'Thumbelina Leigh' is distinguishable from *Lavandula angustifolia* 'Lady' by its smaller overall size, a darker green stem, cylindrical spike shape, purple calyx and more vigorous habit.

'Thumbelina leigh' is distinguishable from 'Hidcote' in having a smaller flower spike and a darker corrola color.

BRIEF DESCRIPTION OF THE DRAWINGS

The accompanying color photographs illustrate the distinguishing characteristics of the new cultivar 'Thumbelina Leigh'.

BOTANICAL DESCRIPTION OF THE PLANT

Figure 1:
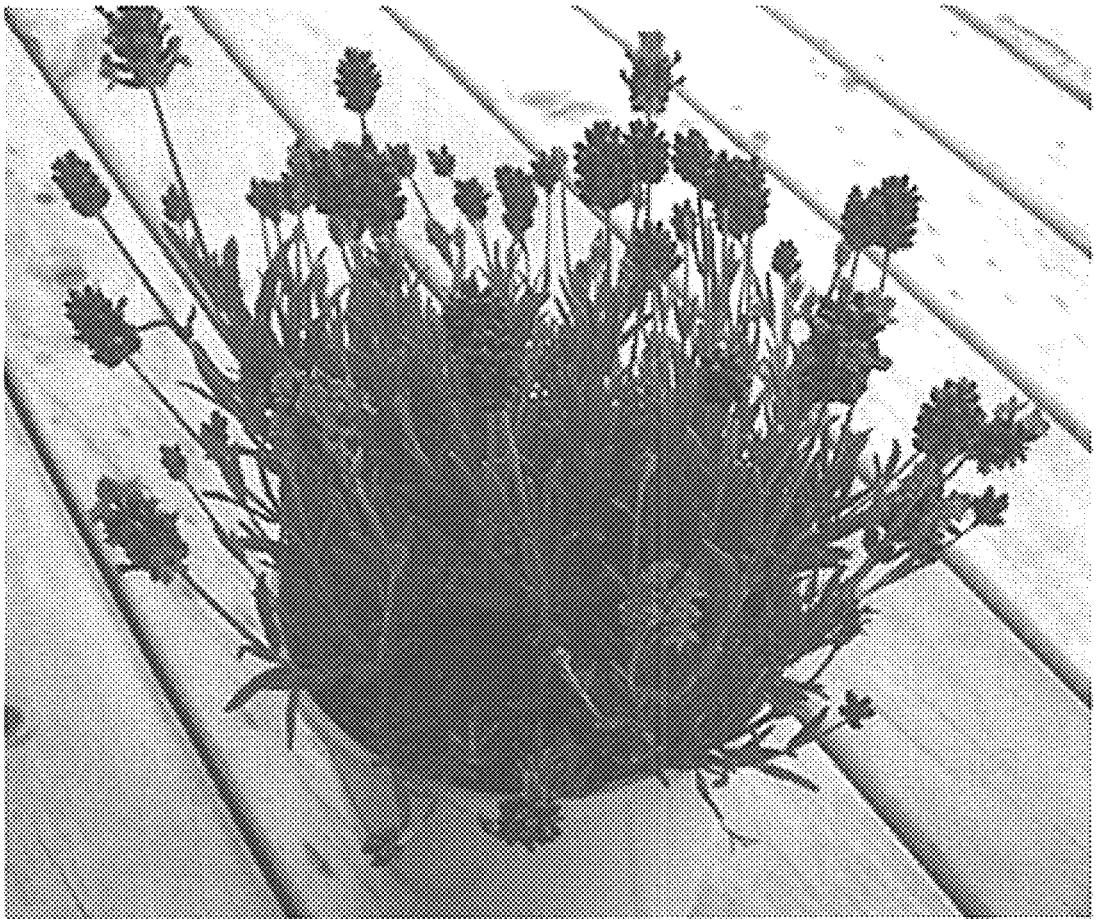
FIG. 1 shows the entire plant, illustrating the plant habit.
Figure 2:
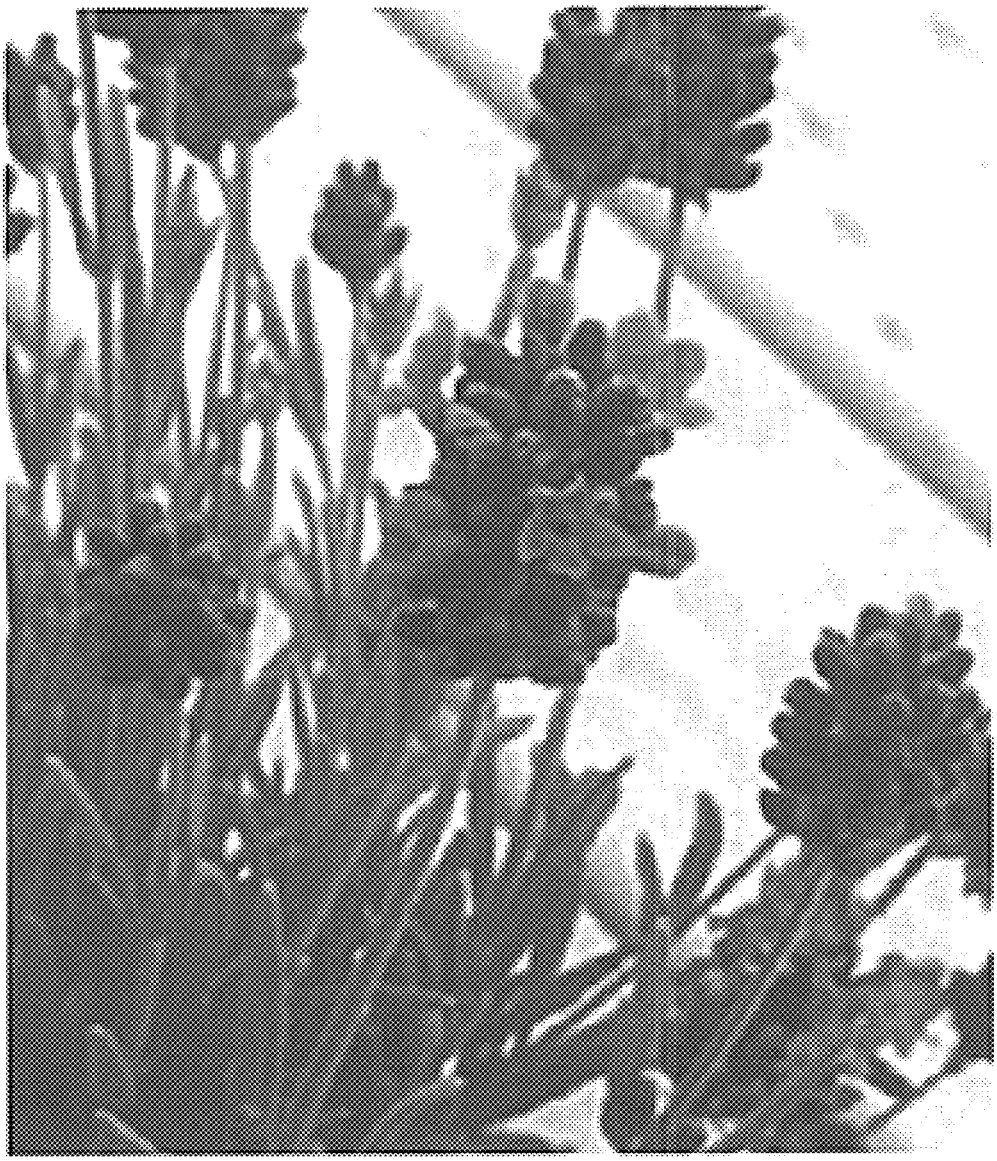
FIG. 2 illustrates the flowers of 'Thumbelina Leigh'. All photographs are taken using conventional photographic techniques and although foliage colors may appear different from actual colors due to light reflectance, they are as accurate as possible by conventional photography.

The following is a detailed description of the *Lavandula angustifolia* cultivar named 'Thumbelina Leigh'. Data was collected in Wairau Valley, Marlborough, New Zealand from 12 month old plants grown in one-gallon containers. Phenotypic differences may be observed with variations in environmental, climatic, and cultural conditions, without however, any difference in genotype. Color determinations are in accordance with the 1995 Royal Horticultural Society Colour Chart except where general color terms of ordinary dictionary significance are used. The growing requirements are similar to the species and no disease problems have been observed.

Botanical classification: *Lavandula angustifolia* 'Thumbelina Leigh'
Common name: Lavender.
Parentage: The parents of 'Thumbelina Leigh' are unknown.
Type: Aromatic perennial shrub.
Use: Ornamental, hedge or back of border plant.
Growth rate: 4 to 8 cm per month.
Habit: Rounded habit, compact with erect, ascending flower spikes.

Height: 40 cm in height.
Spread: 30 cm in width.
Hardiness: Zone 5 to zone 10.
Propagation method: Cuttings.
Root system: Fibrous.
Soil: Plant in well-drained soil.
Light levels: Plant in full scan.
Special needs: None observed.
Time to initiate roots: 18 to 32 days from an unrooted cutting.
Time to develop in a one-gallon container: 6 months from a rooted cutting.
Branching habit: Erect, upright and semi-open.
Seasonal interest: Violet-blue flowers in July and August in the Northern Hemisphere.
Vigor: Vigorous grower.
Stem:
*Shape.*—Cylindrical.
*Surface.*—Puberulent.
*Color.*—143B.
*Size.*—4 mm in diameter, 18 cm in length.
Foliage:
*Arrangement.*—Erect stems of basal leaves.
*Leaf division.*—Simple.
*Apex.*—Acute.
*Base.*—Attenuate.
*Margins.*—Entire.
*Leaf shape.*—Linear.
*Color of mature leaves* (*upper and lower surfaces*).—135B.
*Color of young leaves.*—135B.
*Upper and lower surfaces.*—Puberulent.
*Venation.*—Alternate, visible on lower surface only.
*Foliage fragrance.*—Intense resinous scent of lavender oil.
*Petiole.*—Sessile.
*Length.*—3 cm in length.
*Width.*—0.50 cm in width.
Flower:
*Type of inflorescence.*—Terminal spike.
*Shape of inflorescence.*—Cylindrical-conic fusiform.
*Spike size.*—22 cm in height and 16 mm in width.
*Number of flowers per spike.*—Approximately 50.
*Flower shape.*—Tubular.
*Flower size.*—2 cm in length and 10 mm in diameter.
*Corolla.*—5 petals, fused.
*Corolla color.*—Purple 90A.
*Calyx color.*—Violet 86A.
*Calyx surface.*—Pubescent.
*Bracteoles.*—0.8 mm in length and 0.8 mm in width.
*Bud length.*—12 mm.
*Bud diameter.*—6 mm.
*Bud color.*—90A.
*Fragrance.*—Sweet.
*Blooming period.*—July and August in the Northern Hemisphere.
Reproductive organs: Have not been observed.
Seed production: Has not been observed.

I claim:

1. A new and distinct variety of *Lavandula angustifolia* plant named 'Thumbelina Leigh' as described and illustrated.

* * * * *